United States Patent [19]

Soulal et al.

[11] 4,018,783

[45] Apr. 19, 1977

[54] ESTERS OF METRIZOIC ACID

[75] Inventors: Maurice John Soulal, Long Ditton; Kenneth Utting, Tadworth, both of England

[73] Assignee: Beecham Group Limited, Great Britain

[22] Filed: July 26, 1974

[21] Appl. No.: 492,049

Related U.S. Application Data

[63] Continuation-in-part of Ser. No. 381,023, July 20, 1973, abandoned, which is a continuation-in-part of Ser. No. 178,843, Sept. 8, 1971, Pat. No. 3,795,698.

[30] Foreign Application Priority Data

Sept. 9, 1970  United Kingdom ............ 43070/70
June 28, 1973  United Kingdom ............ 30875/73

[52] U.S. Cl. .................. 260/343.3 R; 260/471 R; 260/472; 424/5
[51] Int. Cl.² ............. C07C 103/46; C07D 307/77
[58] Field of Search ............ 260/471 R, 472, 343.3; 424/5

[56] References Cited

UNITED STATES PATENTS

| | | | |
|---|---|---|---|
| 2,776,241 | 1/1957 | Priewe et al. | 424/5 |
| 3,409,662 | 11/1968 | Larsen | 260/471 R |
| 3,666,800 | 5/1972 | Bernstein et al. | 260/518 A |
| 3,795,698 | 3/1974 | Soulal et al. | 260/471 R |
| 3,812,151 | 5/1974 | Pfeiffer et al. | 260/518 A |

FOREIGN PATENTS OR APPLICATIONS

| | | |
|---|---|---|
| 878,387 | 11/1962 | France |
| 58,307 | 10/1967 | Germany |
| 973,881 | 10/1964 | United Kingdom |

*Primary Examiner*—Richard L. Raymond

[57] ABSTRACT

The phthalide, alkyl, aralkyl, dialkylaminoalkyl and alkylcarbonyloxyalkyl esters of iothalamic acid and metrizoic acid are useful as X-ray contrast agents.

3 Claims, No Drawings

ESTERS OF METRIZOIC ACID

This application is a continuation-in-part of application Ser. No. 381,023, filed July 20, 1973, now abandoned which is continuation-in-part of application Ser. No. 178,843, filed Sept. 8, 1971 now U.S. Pat. No. 3,795,698.

This invention relates to esters of iodine - containing organic acids, which are useful as X-ray contrast agents.

It is known to employ certain iodine - containing compounds as contrast agents in X-ray photography for rendering visible various organs of the body. In particular, U.S. Pat. No. 3,145,197 discloses 5-acetamido-2,4,6,-tri-iodo-N-methylisophthalamic acid (iothalamic acid) of formula (I), wherein $A = -CO.NH.CH_3$:

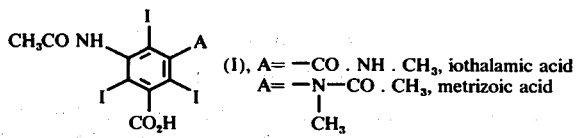

(I), $A = -CO.NH.CH_3$, iothalamic acid
$A = -N-CO.CH_3$, metrizoic acid
            |
           $CH_3$ and lower alkyl esters thereof, as being useful as X-ray contrast agents.

In our British Patent Application No. 43070/70, there are disclosed the acetoxymethyl and pivaloyloxymethyl esters of iothalamic acid.

Metrizoic acid, (I) $A=N(CH_3).CO.CH_3$ has also been disclosed as an X-ray contrast agent.

It has now been found that certain further esters of the acids (I) have improved utility as X-ray contrast agents.

The present invention provides esters of formula

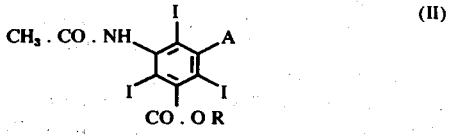

(II)

wherein A is a group of formula $-CO.NH.CH_3$ or $-N(CH_3)CO.CH_3$ and R is a phthalide group, or a straight or branched chain lower alkyl group optionally substituted with an aryl or dialkylamino group, or with a group of formula:

$-O\ CO.R_1$ wherein $R_1$ is a lower alkyl group except that, when A is $-CO.NH.CH_3$, then R is not acetoxymethyl or pivaloyloxymethyl.

In this specification, the term "lower alkyl" means alkyl groups having from 1-8 carbon atoms.

A suitable aryl group is phenyl and the dialkylamino group may be di(lower) alkylamino, such as dimethylamino or diethylamino.

Suitable examples of the lower alkyl groups for R and $R_1$ include methyl, ethyl, n- and iso- propyl, n-, iso, sec- and t-butyl groups.

Preferred values of R are the phthalide group and a group of formula

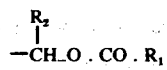

wherein $R_1$ is a $C_{1-6}$ alkyl group and $R_2$ is H or a $C_{1-6}$ alkyl group.

The esters of this invention may be prepared by esterification of the acid (I) with the corresponding alcohol or by using reactive derivatives.

Thus, the invention also provides a process for the preparation of compounds of formula (II) which process comprises reacting compound (I) or a reactive esterifying derivative thereof, with a compound of formula (IV):

R. OH         (IV)

or a reactive esterifying derivative thereof, in which formula R is as defined with respect to formula (II) above.

By the term reactive esterifying derivative in relation to compounds (I) and (IV) above, we mean derivatives of (I) and (IV) which when reacted together take part in a condensation reaction with the consequent formation of an ester linkage of formula (II).

Examples of reactive esterifying derivatives of compound (I) include salts, in particular the sodium, potassium and triethylammonium salts; acid halides, in particular the acid anhydride or mixed anhydrides, for example with a lower alkyl ester of carbonic acid; or the reactive intermediate formed with a carbodiimide or carbonyldiimidazole.

Examples of reactive esterifying derivatives of compound (IV) include halides of formula (IV A):

R. X         (IV A)

wherein X is a halogen atom. Preferred halides are the bromide, chloride and iodide.

Usually it will be found satisfactory to react the sodium, potassium or triethylammonium salt of a compound of formula (I) with a halide of formula (IV A) in a solvent such as dimethyl formamide or acetone.

The invention also includes an X-ray opaque composition comprising a derivative of formula (II), together with a pharmaceutically acceptable carrier.

Primarily such compositions will usually be employed for diagnostic purposes as X-ray contrast agents, especially in bronchography, the delineation of tissue planes, salpinography and transumbilical hepatography. The carriers used are those appropriate for the particular use, and since the derivatives of formula (II) are water-insoluble, they may be conveniently be administered as an aqueous dispersion, an aerosol, in micro-encapsulated form or in an oily solution.

For bronchography the compound may be combined with a non-toxic water-soluble or metabolisable solid carrier e.g. lactose, for purposes of insufflation.

In such a formulation, the contrast agent (II) is suitably in micronised form, that is the particle diameters being less than 50 microns, preferably less than 10 microns. It is also advisable to remove from the formulation, particles having diameters less than 3 microns, which coat the alveoli and thus cloud the picture of the bronchi which are under examination. The carrier, in order to enhance the flow properties of the formulation, normally has particle sizes larger than these of the compound (II), preferably in the range 30–100 microns. It suitably comprises from 0.1 to 10% by weight of the formulation. The composition may also include a small proportion of the sodium salt of the corresponding acid (I), to act as a wetting agent; and the addition of a surfactant is often desirable to assist distribution within the lungs. The dose of inhalable contrast agent composition which is administered is normally in the range 2-20g., preferably about 10g.

The following Examples Illustrate the invention.

EXAMPLE 1

Phthalide ester of
5-acetamido-2,4,6-tri-iodo-N-methyisophthalamic acid
(iothalamic acid.)

63.6g. sodium iothalamate (0.1 mole) was dissolved in 400 ml. dimethylformamide by warming to 50°. To the solution was added a solution of 21.3g 3-bromophthalide (0.1 mole) in 100 ml. dimethylformamide and the mixture stirred at ambient temperature for 24 hours. The reaction mixture was then added to 1500 ml. water with vigorous stirring. After filtering and drying the product was recrystallised from dimethylformamide/water, giving the required ester in 66% yield melting point 280°–281° C(d).

Analysis: $C_{19}H_{13}I_3N_2O_6$ requires: C,30·59;H,1.76 N 3.76; I,51.03%: found: C,30.44;H,1.74;N,3.89; I,50.75%

EXAMPLE 2 n-Pentyl iothalamate

To a solution of sodium iothalamate (6.36 g., 0.01 mole) in dimethylformamide (50 ml.) was added 1-iodopentane (1.98 g., 0.01 mole) and the mixture stirred for 5 hours. After reducing the volume to ca. 15 ml. in vacuo, water was added and the product recrystallised from ethanol/water. The title compound was obtained in 53% yield.

m.p. 262°–5° C,
$C_{16}H_{19}I_3N_2O_4$ requires: C, 28.08; H, 2.80; N, 4.90: I, 55.67%; found: C, 28.10— H, 2.81; N, 4.01; I, 56.00%

EXAMPLE 3 n-Hexyl iothalamate

The procedure of Example 2, using 1-bromohexane in place of 1-iodopentane gave the title compound, m.p. 263°–5°C (from ethanol/water) in 65% yield.

$C_{17}H_{21}I_3N_2O_4$ requires C, 29.25; H, 3.03; N, 4.01; I, 54.56%; found: C, 29.35: H, 3.10; N, 3.92; I, 55.18%

EXAMPLE 4 n-octyl iothalamate

The procedure of Example 2, using 1-bromooctane in place of 1-iodopentane gave the title compound, m.p. 258° C (from ethanol/water) in 68% yield.

$C_{19}H_{25}I_3N_2O_4$ requires: C, 31.41; H, 3.47; N, 3.86; I, 52.40%; found: C, 31.38; H, 3.54; N, 3.57; I, 54.02%

EXAMPLE 5

Benzyl iothalamate

Sodium iothalamate (6.36 g 0.01 mole) was dissolved, with stirring, in dimethylformamide (30 ml) at 50° C. To the stirred solution was added-benzyl bromide (1.7 g 0.01 mole) in dimethylformamide (10 ml), and the resulting mixture stirred 24 hr. at ambient temperature. The reaction mixture was then added to water (400 ml) and the resulting solid filtered off. Benzyl iothalamate was obtained in 70% yield m.p. 295° C (d) after recrystallisation from ethanol.

EXAMPLE 6

α-Pivaloyloxyethyl iothalamate

Sodium iothalamate (80 g., 0.125 mole) was dissolved in dimethylformamide (500 ml.) at 50°. To this solution was added α-bromoethylpivalate (26.1 g., 0.125 mole) in one portion and the mixture stirred for 2½ hours, with no external heating. The reaction mixture was then poured into water (1500 ml.) with stirring and the somewhat sticky white solid recrystallised from DMF/H₂O. α-Pivaloyloxyethyl iothalamate was obtained in 53% yield, m.p. 255° C.

$C_{18}H_{21}I_3N_2O_6$ requires: C, 29.25; H, 2.83; N, 3.77; I, 51.25%; found: C, 29.21; H. 2.91; N, 3.67; I, 51.44%

EXAMPLE 7

α-Acetoxyethyl iothalamate

Sodium iothalamate and αbromoethyl acetate were reacted in an identical manner, yielding α-acetoxyethyl iothalamate in 62% yield, m.p. 243–4° C.

$C_{15}H_{15}I_3N_2O_6$ requires: C, 25.70; H, 2.15; N, 4.00 I, 54.45%; found: C, 25.80; H, 2.20; N, 4.27; I, 54.04%

EXAMPLE 8

Dimethylaminoethyl iothalamate

To a stirred mixture of methyl iothalamate (12.6 g., 0.02 moles) and 2-dimethylaminoethanol (50 ml.) in 80°–100° petroleum spirit (100 ml.) was added a solution of sodium (0.025 g., 0.001 g. atom) in methanol (1 ml., 0.025 moles) during ca. 5 hours. Methanol was removed by azeotropic distillation during ca. 5 hours. A further quantity of dimethylaminoethanol (75 ml.) was added and the azedropic distillation continued overnight. After cooling, the white solid was filtered off, washed with water to remove excess dimethylaminoethanol and dried. The product was recrystallised from dimethylformamide/water (1:1) giving dimethylaminoethyl iothalamate, m.p. 295°–6° C. in 30% yield.

$C_{15}H_{18}I_3N_3O_4$ requires; C, 26.30; H, 2.50; N, 6.14; I, 55.70%; found: C, 26.00; H, 2.58; N, 5.98; I, 56.12%.

EXAMPLE 9

Phthalide ester of metrizoic acid

To a solution of sodium metrizoate (6.5 g., 0.01 mole) in dimethylformamide (DMF, 25 ml) was added a solution of 3-bromophthalide (2.14 g., 0.01 mole) in DMF (25 ml.). After stirring overnight at ambient temperature, the volume was reduced to ca. 15 ml. in vacuo. Addition of water precipitated a white solid which was recrystallised from ethanol/water to give the title compound.

m.p. 200° C
$C_{20}H_{15}I_3N_2O_6$ requires: C, 31.61; H, 1.99; N, 3.69; I, 50.09%; found: C, 31.43; H, 2.05; N, 3.49; I, 48.17%.

EXAMPLE 10

Pivaloyloxymethyl metrizoate

Sodium metrizoate (65 g., 0.1 mole) was dissolved in DMF (500 ml.) at 50° C. The solution was stirred and bromomethyl pivalate (19.9 g., 0.1 mole) added in one portion. The mixture was stirred overnight at ambient temperature, then evaporated in vacuo to give a viscous oil. This was triturated with water (500 ml.) to yield a white solid. Pivaloyloxymethyl metrizoate was obtained in 54% yield, m.p. 233°–4° C, after recrystallisation from methanol.

$C_{18}H_{21}I_3N_2O_6$ requires C, 29.13; H, 2.85; N, 3.78; I, 51.30%; found: C, 29.33; H, 2.89; N, 3.66; I, 51.03%

EXAMPLE 11

Benzyl metrizoate

Using the procedure of Example 10, sodium metrizoate and benzyl bromide were reacted in equimolar (0.1 mole) quantities yielding benzyl metrizoate in 71% yield, m.p. 253°–5° C, from DMF/water.

$C_{19}H_{17}I_3N_2O_4$ requires C, 31.78; H, 2.39; N, 3.90; I, 53.02%; found: C, 31.73; H, 2.48; N, 4.16; I, 53.06%.

EXAMPLE 12 n-Hexylmetrizoate

Using the procedure of Example 10, sodium metrizoate and 1-bromohexane were reacted in equimolar (0.01 mole) quantities yield n-hexylmetrizoate in 50% yield, m.p. 156° C, from DMF/water.

$C_{18}H_{23}I_3N_2O_4$ requires: C, 30.36; H, 2.26; N, 3.93 I, 53.46%; found: C, 30.54; H, 3.11; N, 3.71; I, 54.00%.

EXAMPLE 13

α-Pivaloyloxyethyl metrizoate

To a solution of sodium metrizoate (6.5 g., 0.01 mole) in DMF (50 ml.) at 50° C was added α-bromoethyl pivalate (2.1 g., 0.01 mole) and the mixture stirred for 2 hours with no additional heating. The mixture was then poured into water (200 ml.) α-Pivaloyloxyethyl metrizate was obtained in 60% yield. m.p. 210° C, from DMF/water.

$C_{19}H_{23}I_3N_2O_6$ requires: C, 30.20; H. 3.04; N, 3.71; I, 50.40%; found: C, 30.08; H, 3.25; N, 3.68 I, 50.35%.

EXAMPLE 14

An X-ray opaque composition was prepared as follows

| | |
|---|---|
| phthalide ester of iothalamic acid (particle size 3–6μ) | 9.4g. |
| sodium iothalamate | 0.1g. |
| lactose (particle size 30–80μ) | 0.5g. |
| | 10.0g |

What is claimed is:
1. Phthalide ester of metrizoic acid.
2. Pivaloyloxymethyl metrizoate.
3. α-Pivaloyloxyethyl metrizoate.

* * * * *